United States Patent [19]

Aoyagi

[11] 4,450,278
[45] May 22, 1984

[54] INTERMEDIATES FOR 1-METHYL-3,4-DIHALO-5-THIO-(2-HYDROXYETHYL)-PYRAZOLE

[75] Inventor: Edward I. Aoyagi, Petaluma, Calif.

[73] Assignee: Chevron Research Company, San Francisco, Calif.

[21] Appl. No.: 393,214

[22] Filed: Jun. 28, 1982

[51] Int. Cl.³ .......................................... C07D 231/18
[52] U.S. Cl. ................................................ 548/376
[58] Field of Search ....................................... 548/376

[56] References Cited

U.S. PATENT DOCUMENTS 3,849,106 11/1974 Kornis et al. ...................... 548/376
4,044,013 8/1977 Cross et al. ........................ 548/376

*Primary Examiner*—Richard Raymond
*Attorney, Agent, or Firm*—S. R. LaPaglia; T. G. DeJonghe; S. L. Biggs

[57] ABSTRACT

Compounds of the formula:

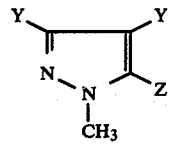

wherein Y is chloro or bromo and Z is chloro, bromo or the group —SCH₂CH₂OH are intermediates in the synthesis of corresponding 1-methyl-3,4-dihalo-5-substituted thio, sulfinyl or sulfonyl pyrazole fungicides.

2 Claims, No Drawings

INTERMEDIATES FOR 1-METHYL-3,4-DIHALO-5-THIO-(2-HYDROXYETHYL)-PYRAZOLE

BACKGROUND OF THE INVENTION

This invention relates to 1-methyl-3,4,5-trihalopyrazoles and 1-methyl-3,4-dihalo-5-thio-(2-hydroxyethyl) pyrazoles and to methods of preparing such compounds and to intermediates therefor. The invention also relates to processes for converting the above compounds to such compounds having fungidical activity.

Fungicidal and algicidal 1-methyl-3,4-dihalo-5-substituted thio-, sulfinyl-, and sulfonyl-pyrazoles for which the compounds of this invention are intermediates are disclosed in my commonly assigned U.S. patent application Ser. No. 393,213, filed June 28, 1982, "Fungicidal and algicidal 1-methyl-3,4-dihalo-5-substituted thio-, sulfinyl-, or sulfonyl-pyrazoles".

SUMMARY OF THE INVENTION

The compounds of the present invention may be represented by the following formula:

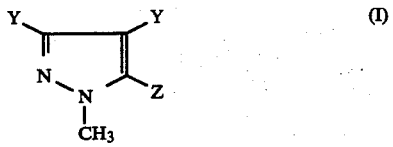

wherein Y is chloro or bromo and Z is chloro, bromo or the group —SCH$_2$CH$_2$OH.

The intermediates of Formula I wherein Z is chloro or bromo are used in the synthesis of the intermediates of Formula I wherein Z is the group —SCH$_2$CH$_2$OH.

The compounds of this invention are used in the synthesis of 1-methyl-3,4-dihalo-5-substituted thio-, sulfinyl- or sulfonyl-pyrazole compounds having the following formula:

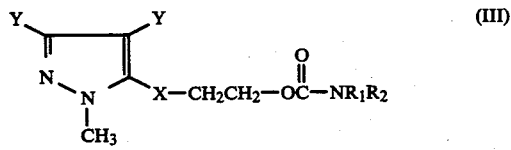

wherein Y is chloro or bromo; X is —S—, —SO—, or —SO$_2$; and R$_1$ and R$_2$ are independently hydrogen alkyl, cycloalkyl, lower alkenyl of 3 or more carbon atoms, alkylene carbalkoxy or aryl or aralkyl optionally substituted with one or two substituents, each independently selected from halogen, nitro, cyano, lower alkyl, lower alkoxy, trihalo-substituted methyl and phenoxy which are fungicidal or useful as intermediates in the synthesis of fungicidal compounds.

Among other factors, the present invention is based on my finding that these novel intermediates are useful in the synthesis of 1-methyl-3,4-dihalo-5-sulfinyl or sulfonyl substituted pyrazole compounds of Formula III which are surprisingly effective as fungicides and, in many cases, also as algicides. The compounds of Formula III as a group are especially effective against Grape Downy Mildew, and also against Tomato Late Blight and Rice Blast. The sulfides of Formula III are useful as intermediates in the synthesis of the sulfoxides and sulfones. In addition, some of the sulfides of Formula III show fungicidal and/or algicidal activities.

Representative R$_1$ and R$_2$ groups include methyl, isopropyl, n-butyl, isobutyl, tert-butyl, n-hexyl, n-octyl, allyl, pent-3-yl, phenyl, p-chlorophenyl, 3,4-dichlorophenyl, 3,5-dichlorophenyl, m-methylphenyl, p-methoxyphenyl, m-methoxyphenyl, p-butylphenyl, m-trifluoromethylphenyl, m-phenoxyphenyl, methylenecarbethoxy and cyclohexyl.

Preferred are compounds where X is —SO$_2$— and R$_1$ is alkyl, cycloalkyl, alkenyl of 3 to 6 carbon atoms, phenyl or substituted phenyl and R$_2$ is hydrogen. Particularly preferred substituted phenyl R$_1$ groups include those substituted with one to three substituents selected from halogen, lower alkyl, lower alkoxy, trihalo-substituted methyl and phenoxy.

DEFINITIONS

As used herein, the following terms have the following meanings, unless expressly stated to the contrary.

The term "alkyl" refers to both straight- and branched-chain alkyl groups. The term "lower alkyl" refers to both straight- and branched-chain alkyl groups having a total of from 1 to 6 carbon atoms and includes primary, secondary and tertiary alkyl groups. Typical lower alkyls include, for example, methyl, ethyl, n-propyl, isopropyl, n-butyl, isobutyl, t-butyl, n-pentyl, n-hexyl, and the like.

The term "alkylene" refers to the group —(CH$_2$)$_m$— wherein m is an integer greater than zero. Typical alkylene groups include methylene, ethylene, propylene and the like.

The term "alkenyl" refers to unsaturated alkyl groups having a double bond [e.g., CH$_3$CH=CH—(CH$_2$)—] and includes both straight- and branched-chain alkenyl groups. "Lower alkenyl" refers to groups having a total of from 3 to 6 carbon atoms. Typical lower alkenyl groups include, for example, propenyl, but-3-enyl, hex-4-enyl, 2-methylpent-4-enyl, and the like.

The term "halo" or "halogen" refers to the groups fluoro, chloro, bromo and iodo.

The term "alkoxy" refers to the group R'O— wherein R' is alkyl. The term "lower alkoxy" refers to alkoxy groups having from 1 to 6 carbon atoms; examples include methoxy, ethoxy, hexoxy, and the like.

The term "hydroxy alkyl" refers to the group —R'—'OH wherein R" is branched or unbranched alkylene and the hydroxyl can be on a primary, secondary or a tertiary carbon. Examples include hydroxy ethyl and 2-hydroxypropyl and 2-hydroxy-2-methyl butyl.

The term "aryl" refers to aryl groups having from 6 to 10 carbon atoms and includes, for example, phenyl, p-chlorophenyl, m-methylphenyl, p-butylphenyl, and m-trifluoromethylphenyl.

The term "arylalkyl" refers to an alkyl group of 1 to 4 carbons substituted with an aryl group of from 6 to 10 carbons and includes, for example, benzyl, p-chlorobenzyl, -methylbenzyl and 2-phenylethyl.

The term "alkylene carbalkoxy" refers to the group

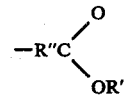

wherein R' is alkyl and R" is alkylene. Examples include carbethoxy methyl and carbmethoxy ethyl.

The term "pyrazole" refers to the

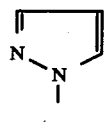

group. The conventional numbering system for this group is shown below.

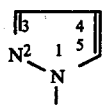

DETAILED DESCRIPTION OF THE INVENTION

The compounds of this invention may be prepared according to the following reaction sequences.

Where Z is chloro or bromo:

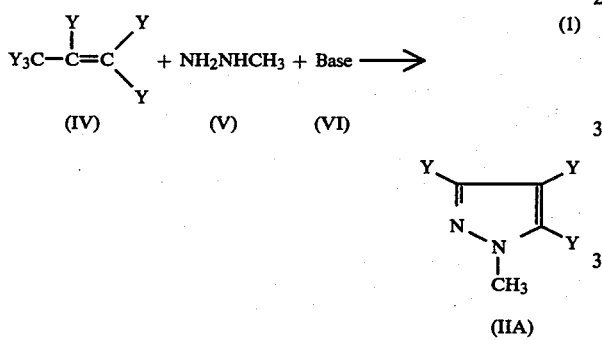

wherein Y is chloro or bromo.

Reaction (1) is carried out by reacting (IV) and (V) in the presence of base (VI). Suitable bases include organic or inorganic bases, such as $K_2CO_3$, $Na_2CO_3$, triethylamine and the like. It is preferred to add an excess of (V) and (VI) per equivalent of (IV) for ease of workup. It is especially preferred to add at least 3 and more preferably 5 equivalents of (VI) per equivalent of (IV). Reaction (1) may be carried out by adding (VI) with stirring to a solution of (IV) and solvent, followed by the slow addition of (V). For convenience, the reaction is carried out at ambient pressure. Suitable solvents include inert organic solvents such as toluene, benzene, dimethoxy ethane, tetrahydrofuran and the like. The Product (IIA), a low-melting white solid, is isolated by conventional procedures such as extraction, chromatography, and recrystallization.

Where Z is hydroxyethylthio ($-SCH_2CH_2OH$), the intermediates of this invention are made according to the following reaction sequence:

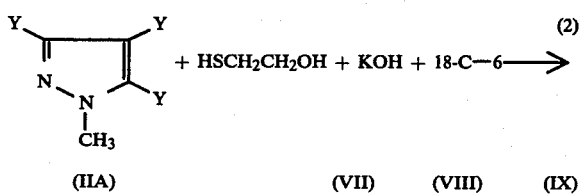

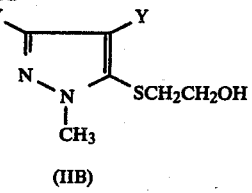

wherein Y is as previously defined.

Reaction (2) is carried out by adding (IIA) to (VII) and (VIII) in DMSO (dimethyl sulfoxide) and heating the resulting mixture for about 1 to about 24 hours. A catalytic amount of crown ether (IX) (18-crown-6) may be used to facilitate the reaction. Reaction (2) may also be carried out in solvents such as DMF (dimethyl formamide) and HMPA (hexamethyl phosphoramide). Water is added to the reaction mixture, and Product (IIB) is isolated by conventional techniques such as extraction, filtration, chromatography, or distillation.

The sulfide compounds of Formula (III), wherein $R_2$ is hydrogen, are made from the hydroxyethyl-substituted compound of Formula I (IIB) according to the following reaction sequence:

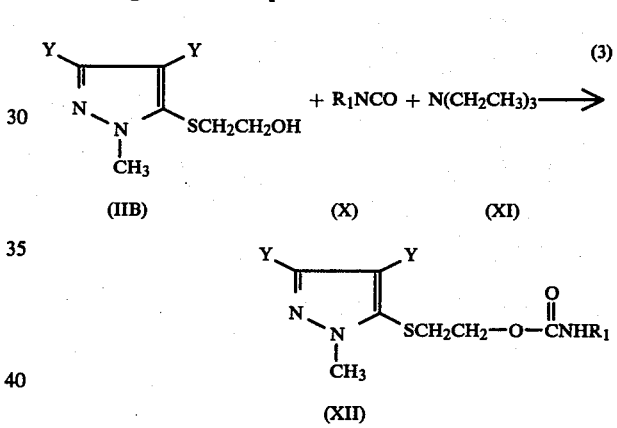

wherein $R_1$ is as defined in conjunction with Formula (III). The isocyanate compounds (X) used in synthesizing (XII) are produced by methods well known to those skilled in the art.

Reaction (3) is conducted by stirring (IIB), (X), and a few drops of (XI) in methylene chloride for about ½ to about 24 hours. Alternatively, after addition of the reactants, the reaction mixture may be refluxed for about ½ hour to about 24 hours. Product (XII) is isolated by conventional procedures or a combination thereof such as extraction, filtration, chromatography, recrystallization, and the like.

The sulfide compounds of Formula III wherein $R_2$ is not hydrogen are made from the hydroxyethyl-substituted compound (IIB) according to the following reaction sequence:

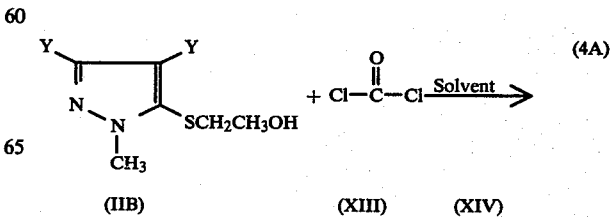

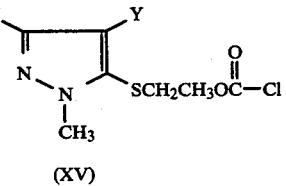

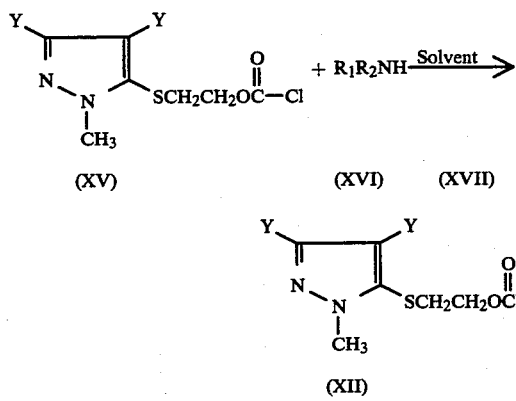

Reaction (4A) is conducted by the dropwise addition of a solution of (IIB) dissolved in (XIV) to XIII also dissolved in solvent followed by prolonged stirring (from about 2 to about 24 hours), to give XV. Suitable solvents (XVI) include inert organic solvents such as toluene, methylene chloride, chloroform and the like. Product XV may be used in Reaction (4B) without further isolation.

Reaction (4B) is conducted by adding (XVI) to a stirred solution of (XV) in (XVII). The reaction mixture is then stirred from about 1 to about 24 hours. Product (XII) is then isolated by conventional procedures, or a combination thereof, such as extraction, chromatography and the like.

The sulfinyl or sulfonyl compounds of Formula (III) corresponding to Products (XII) may be made from the sulfide compounds by selective oxidation of the thio group according to the following reaction scheme:

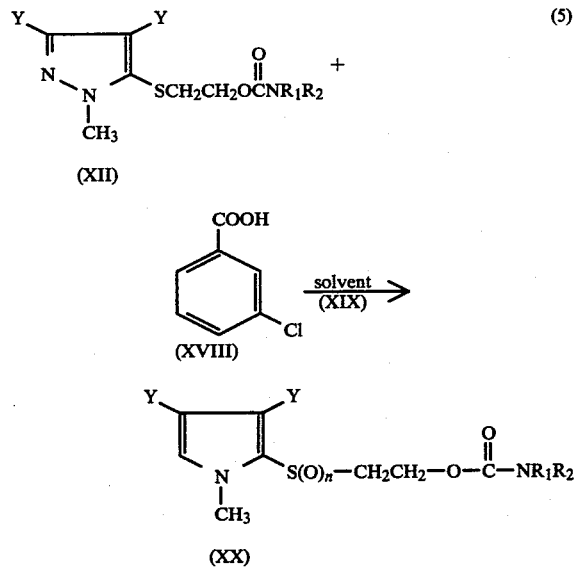

wherein n is 1 or 2 and Y, $R_1$ and $R_2$ are as previously defined.

Reaction (5) is conducted by stirring (XII) in (XIX), followed by the addition of (XVIII) in portions. The reaction mixture is stirred at ambient temperature for about 2 to about 24 hours and may optionally be refluxed for about 2 to about 8 hours. The Product (XX) is then isolated by conventional procedures such as extraction, filtration, chromatography, recrystallization, and the like. Although chloroform is the preferred solvent (XIX), other suitable solvents include other chlorinated hydrocarbon solvents such as methylene chloride and other inert organic solvents. It is well established that peroxides such as meta-chloro-perbenzoic acid (MCPBA) (XVIII) and the like oxidize thio derivatives (such as XII) to the corresponding sulfoxide or sulfone. To obtain the sulfinyl compound (n=1) corresponding to (XII), (XVIII) is added in the ratio of approximately one equivalent (XVIII) per equivalent (XII). Addition of (XVIII) in the ratio of about two or more equivalents (XVIII) per equivalent (XII) yields the corresponding sulfone.

The sulfinyl and sulfonyl compounds which are synthesized from the intermediates of this invention are useful for controlling fungi, particularly plant fungal infections and late blights, including Grape Downy Mildew, Tomato Late Blight and Rice Blast. However, some fungicidal compounds of Formula III may be more fungicidally active than others against particular fungi. The sulfide compounds of Formula III are used as intermediates in the synthesis of the corresponding sulfoxides and sulfones of Formula III. In addition, many of the sulfide compounds of Formula III exhibit fungicidal activity. However, in general, the sulfoxide and sulfone compounds of Formula III exhibit a greater fungicidal activity and a wider range of fungicidal activities than the analogous sulfides. Also, the sulfonyl compounds of Formula III generally exhibit greater fungicidal activity than the corresponding sulfinyl compounds.

Many of the compounds of Formula III synthesized from the intermediates of this invention are also useful for controlling microbiological organisms such as algae, bacteria, molds and occasionally aquatic weeds which foul aqueous industrial effluents and cooling streams, such as those occurring in the paper and food processing industries. They may also be used to control such organisms in other aqueous bodies such as lakes, streams, canals, pools, and the like.

In addition, some of the compounds of Formula III synthesized from the intermediates of this invention exhibit herbicidal activity, generally in post-emergent applications. For post-emergent applications, the herbicidal compounds will be applied directly to the foliage and other plant parts. Generally, those compounds exhibiting herbicidal activity are effective against weed grasses as well as broad-leaved weeds. Some compounds may be selective with respect to the type of application and/or type of weed.

A further understanding of my invention may be had from the following non-limiting examples.

EXAMPLES

Preparation of 1-methyl-3,4,5-trichloro-pyrazole

To a rapidly stirred mixture of 11.4 g (0.04 mole) hexachloropropane and 16.6 g (0.012 mole) potassium carbonate in 100 ml toluene, 1.85 g (0.04 mole) methyl hydrazine was added slowly. The addition was slightly exothermic and the color of the reaction mixture turned to light orange-brown. The reaction mixture was then stirred overnight at ambient temperature. The reaction mixture was then heated to about 80° C. for about three hours and then cooled. A powdery solid appeared in the mixture. The mixture was filtered and the solids washed with ethyl ether.

The ethyl ether washings and reaction mixture filtrate were combined and stripped under reduced pressure and heat to give a black oil. The oil was chromatographed on a silica column, eluting first with hexane (which elutes unreacted starting materials) and then with methylene chloride. The methylene chloride eluate was stripped to give a pale yellow oil which solidified upon standing. Recrystallization from hexane gave 2.5 g of the product, a white solid with a melting point of 33°–35° C.

Elemental analysis for $C_4H_3Cl_3N_2$ showed: calculated %C 25.90, %H 1.63, and %N 15.11; found %C 23.67, %H 1.65, and %N 13.8.

By following the above procedure, but starting with 114 g (0.4 mole) of hexachloropropene and the corresponding proportions of the other reactants, 32.9 g of the product was prepared, a 34% yield (of theoretical).

EXAMPLE 1A

Preparation of 1-methyl-3,4,5-trichloro-pyrazole

To a stirring solution of 250 g (1 mole) of hexachloropropene in 250 ml toluene, there was added 94.4 g (2.05 moles) of methyl hydrazine dropwise. The temperature of the reaction mixture was maintained in the range of about 50° to about 60° C. by the use of external cooling. When the addition of methyl hydrazine was complete, the reaction mixture was cooled to room temperature and 276 g (2 moles) of potassium carbonate was added. The resulting mixture was carefully heated first to about 60° C., then gradually to about 85° to 90° C. Heating was carefully monitored to control occasional exotherm and degassing. After about three hours, the heat source was removed and the reaction mixture was allowed to cool to room temperature. The reaction mixture was diluted with about 500 ml ice water and extracted with methylene chloride. The organic layer (containing the product) was washed twice with water, dried over magnesium sulfate and concentrated on a rotovac to give a red oil (about 275 ml). The red oil was dissolved in hexane and filtered through a short silica column twice to give 133 g of a yellow oil which solidified. Spectra of the solid were identical to those of the product of Example 1.

EXAMPLE 2

Preparation of 1-methyl-3,4-dichloro-5-(2-hydroxyethyl) thio pyrazole

To a mixture of 26.5 g (0.34 moles) 2-mercaptoethanol, 19 g of 85% potassium hydroxide, and a few drops of 18-Crown-6 in 250 ml of DMSO, 60 g (0.32 moles) 1-methyl-3,4,5-trichloro pyrazole (product of Example 1 or 1A) were added in portions. When the addition was complete, the reaction mixture was heated to 140° C. for 1 day. The cooled reaction mixture was diluted with water and extracted with ether. The oganic phase was washed four times with 200 ml water per time, dried and stripped. The crude product was chromatographed on a silica gel column. The product, 1-methyl-3,4-dichloro-5-(2-hydroxyethyl) thio pyrazole, was eluted from the column with ethyl acetate, yielding 27.7 g (37.7% yield) of a yellow oil.

Elemental analysis for $C_6H_8Cl_2N_2OS$ showed: calculated %C 31.73, %H 3.55, and %N 12.34; found %C 36.98, %H 3.77, and %N 12.60.

EXAMPLE 3

Preparation of

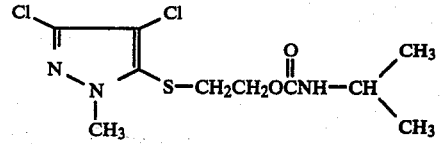

To a mixture of 7.0 g (31 mmoles) 1-methyl-3,4-dichloro-5-(2-hydroxyethyl) thio pyrazole (product of Example 2) and 5.2 g (61 mmoles) isopropyl isocyanate in 25 ml methylene chloride, a few drops (approximately 1 ml) of triethylamine were added. The resulting mixture was then refluxed for 7 hours. Solvent (methylene chloride), triethylamine, and excess isopropyl isocyanate were removed on a rotovac. The remaining material was diluted with toluene and filtered. The toluene filtrated was diluted with hexane and the precipitated solid was removed by filtration. The precipitate was recrystallized from methylene chloride-hexane to give a white solid with a melting point of 58° C. to 59° C.

Elemental analysis for $C_{10}H_{15}Cl_2N_3O_2S$ showed: calculated %C 38.47, %H 4.84, and %N 13.46; found %C 39.96, %H 5.19, and %N 13.97.

EXAMPLE 4

Preparation of

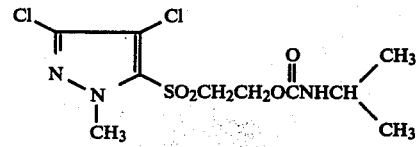

To a stirred mixture of 5 g (16 mmoles) of the product of Example 3 in 100 ml chlorform, 6.8 g (35.2 mmoles) of 90% m-chloroperoxybenzoic acid was added in portions. The reaction mixture was stirred at ambient temperature for 1 hour and then refluxed for 2 hours. An additional 3.4 g of m-chloroperoxybenzoic acid was added to the reaction mixture and the reaction mixture was refluxed for 3 hours. The reaction mixture was cooled and filtered. The filtrate was washed first with a saturated sodium carbonate solution, followed by water. The chloroform phase was dried with magnesium sulfate and stripped to give a white solid. Recrystallization of the solid from methylene chloride-hexane gave 4.5 g of a white solid with a melting point of 111° C. to 117° C.

Elemental analysis for $C_{10}H_{15}Cl_2N_3O_4S$ showed: calculated %C 34.89, %H 4.39, and %N 12.21; found %C 32.41, %H 4.64, and %N 12.58.

EXAMPLE 5

Preparation of

-continued
Preparation of

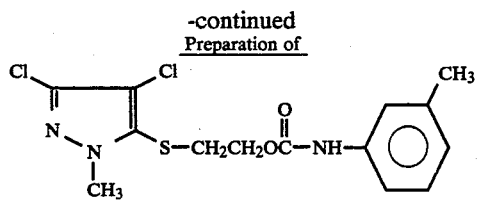

Eight grams (35 mmoles) of 1-methyl-3,4-dichloro-5-(2-hydroxyethyl) thio pyrazole (product of Example 2) and 4.7 g (135 mmoles) of m-tolylisocyanate were treated in a similar manner as in Example 3 to yield 12.6 g of white solid with a melting point of 53°–57° C.

Elemental analysis for $C_{14}H_{15}Cl_2N_3O_2S$ showed: calculated %C 46.80, %H 4.21, and %N 11.70; found %C 46.12, %H 4.46, and %N 9.66.

EXAMPLE 6

Preparation of

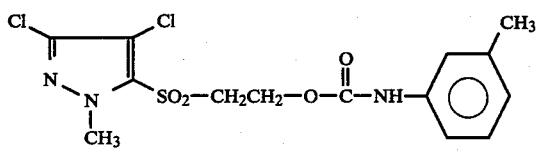

To a stirred mixture of 6.2 g (17 mmoles) of the product of Example 5 in chloroform, 7.71 g (38 mmoles) of 85% m-chloroperoxybenzoic acid was added in portions. The reaction mixture was stirred overnight. Enough additional chloroform was added to dissolve any solids. The chloroform solution was then washed first with saturated sodium carbonate, followed by water. The chloroform phase was partially concentrated and diluted with petroleum ether to precipitate the product as a light brown solid. Recrystallization of the product from methylene chloride-petroleum ether gave 6.75 g of a white solid with a melting point of 116° C. to 118° C.

Elemental analysis for $C_{14}H_{15}Cl_2N_3O_4S$ showed: calculated %C 43.00, %H 3.86, and %N 10.74; found %C 41.92, %H 4.06, and %N 9.06.

EXAMPLE 7

Preparation of

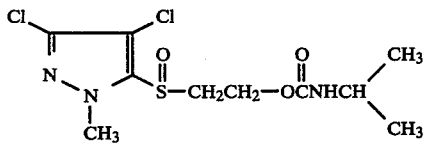

To a stirred solution of 2.1 g (6.7 mmoles) of the product of Example 3 in 50 ml of chloroform, 1.4 g (6.9 mmoles) of 85% m-chloroperbenzoic acid was added. The reaction mixture was stirred at ambient temperature for 20 hours and washed with saturated aqueous sodium bicarbonate solution. The chloroform solution was dried with magnesium sulfate. Removal of chloroform on a rotovac yielded 1.6 g of viscous oil which solidified in standing.

Elemental analysis for $C_{10}H_{15}Cl_2N_3O_3S$ showed: Calculated %C 36.59, %H 4.61, %N 12.80; found %C 36.62, %H 4.76, and %N 12.95.

EXAMPLE 8

Preparation of

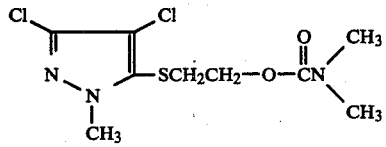

Eight grams (0.0352 mole) of 1-methyl-3,4-dichloro-5-(2-hydroxyethyl) thio pyrazole (product of Example 2) were dissolved in 50 ml toluene. The Example 2-toluene solution was added dropwise with stirring to a solution of 12.5% phosgene in toluene (containing 30.64 g (0.0352 mole) phostene and about 254 ml toluene). The reaction mixture was stirred overnight.

Dimethylamine (1.6 g) was bubbled into the reaction mixture. The mixture was stirred overnight. After a workup such as that described in Examples 3–7, the crude product was chromatographed on silica gel to yield about 0.7 g of pure product and 3.7 g of slightly contaminated product.

Elemental analysis for $C_9H_{13}Cl_2O_2N_3S$ showed: calculated %C 36.25, %H 4.40, and %N 14.09; found %C 35.07, %H 4.51, and %N 13.01.

EXAMPLE 9

Preparation of

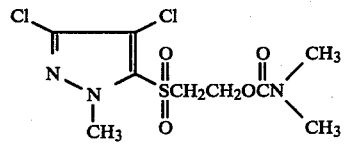

To a stirred mixture of 3.7 g of the product of Example 8, containing a small amount of impurity, in 100 ml chloroform, 7 g of 85% (0.0348 mole) of m-chloroperoxybenzoic acid was added; the resulting mixture was stirred for one day. Thin layer chromatography showed the reaction to be incomplete, so an additional 1 g of the m-chloroperoxybenzoic acid was added and the mixture stirred an additional day. The chloroform solution was then washed twice with a saturated aqueous sodium bicarbonate solution and stripped to give an oil. The oil was chromatographed on silica gel. The product eluted with 10% ethyl acetate in methylene chloride. Two grams of a viscous light yellow oil were obtained.

Elemental analysis for $C_9H_{13}Cl_2O_4N_3S$ showed: calculated %C 32.73, %H 3.97, and %N 12.73; found %C 32.82, %H 4.01, and %N 12.18.

What is claimed is:

1. A compound of the formula:

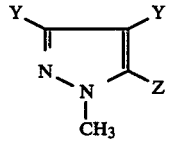

wherein Y is chloro or bromo, and Z is the group —$SCH_2CH_2OH$—.

2. The compound according to claim 1 wherein Y is chloro.

* * * * *